(12) United States Patent
He et al.

(10) Patent No.: US 11,874,272 B2
(45) Date of Patent: Jan. 16, 2024

(54) INHIBITION OF SWEAT MALODOR

(71) Applicant: FIRMENICH SA, Satigny (CH)

(72) Inventors: Xiu-Feng He, Shanghai (CN); Lily Ji-Xiu Zhang, Shanghai (CN)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 16/757,983

(22) PCT Filed: Jan. 9, 2019

(86) PCT No.: PCT/EP2019/050445
§ 371 (c)(1),
(2) Date: Apr. 21, 2020

(87) PCT Pub. No.: WO2019/137956
PCT Pub. Date: Jul. 18, 2019

(65) Prior Publication Data
US 2020/0340975 A1    Oct. 29, 2020

(30) Foreign Application Priority Data

Jan. 10, 2018  (WO) ............... PCT/CN2018/072100

(51) Int. Cl.
*G01N 33/50* (2006.01)
*G01N 1/40* (2006.01)
(Continued)

(52) U.S. Cl.
CPC ............ *G01N 33/50* (2013.01); *G01N 1/405* (2013.01); *G01N 30/06* (2013.01);
(Continued)

(58) Field of Classification Search
CPC .................................................. G01N 33/50
See application file for complete search history.

(56) References Cited

U.S. PATENT DOCUMENTS 4,380,625 A * 4/1983 Stadler ................. C07H 15/234
536/16.8
5,538,719 A * 7/1996 Preti ....................... A61Q 15/00
424/65

(Continued)

FOREIGN PATENT DOCUMENTS

CN        104729887 A     6/2015
JP      2004309454 A    11/2004
(Continued)

OTHER PUBLICATIONS

International Search Report and Written Opinion for corresponding International Application No. PCT/EP2018/050445, dated Apr. 24, 2019,11 pages.

(Continued)

*Primary Examiner* — Jamel E Williams
*Assistant Examiner* — Alex T Devito
(74) *Attorney, Agent, or Firm* — Armstrong Teasdale LLP

(57) ABSTRACT

The present disclosure related to a method for screening compounds having the ability to prevent, treat or reduce malodor development on body surfaces. In particular, the method screens for compounds having the ability of preventing sweat malodor development caused by malodor causing volatile acid compounds and/or malodor causing volatile sulphur compounds. The present disclosure is based on a sensitive analytical method to determine the presence of the precursors of malodor causing volatile acid compounds and/or malodor causing volatile sulphur compounds present in sweat, which are metabolised by bacteria, such as, for example, *Cornebacteria* or *Staphylococci* to malodor causing volatile acid compounds and malodor causing volatile sulphur compounds.

19 Claims, 8 Drawing Sheets

(51) Int. Cl.
*G01N 30/06* (2006.01)
*G01N 30/72* (2006.01)
*G01N 33/497* (2006.01)
G01N 30/02 (2006.01)
G01N 30/12 (2006.01)

(52) U.S. Cl.
CPC ....... *G01N 30/7206* (2013.01); *G01N 33/497* (2013.01); *G01N 2001/4061* (2013.01); *G01N 2030/025* (2013.01); *G01N 2030/128* (2013.01); *G01N 2033/4975* (2013.01)

(56) References Cited

U.S. PATENT DOCUMENTS

| | | | | |
|---|---|---|---|---|
| 5,801,297 | A * | 9/1998 | Mifsud | G01N 33/0031 73/31.05 |
| 2004/0039208 | A1* | 2/2004 | Chen | C07D 209/44 564/434 |
| 2006/0160240 | A1* | 7/2006 | Hasegawa | G01N 33/497 436/166 |
| 2008/0190218 | A1* | 8/2008 | Riazanskaia | G01N 1/22 73/864 |
| 2009/0081795 | A1* | 3/2009 | Furton | G01N 1/405 436/63 |
| 2010/0132485 | A1* | 6/2010 | Erez | A61B 5/4266 73/864.63 |
| 2010/0184122 | A1 | 7/2010 | Yabuki et al. | |
| 2010/0203652 | A1* | 8/2010 | Harvey | B01J 20/3293 436/518 |
| 2012/0052031 | A1 | 3/2012 | Troccaz et al. | |
| 2015/0276690 | A1* | 10/2015 | Hudalla | B01J 20/205 73/23.39 |

FOREIGN PATENT DOCUMENTS

| | | |
|---|---|---|
| JP | 2005017272 A | 1/2005 |
| WO | 2006079934 A2 | 8/2006 |

OTHER PUBLICATIONS

Natsch, A. et al., A specific bacterial aminoacylase cleaves odorant precursors secreted in the human axilla, Journal of Biological Chemistry, Feb. 21, 2002, vol. 278, No. 8, pp. 5718-5727.

* cited by examiner

INHIBITION OF SWEAT MALODOR

CROSS REFERENCE TO RELATED APPLICATIONS

This application is a U.S. National Phase Application of PCT/EP2019/050445, filed Jan. 9, 2019, which claims priority to International Application No. PCT/CN2018/072100, filed on Jan. 10, 2018, the entire contents of which are hereby incorporated by reference in their entirety.

FIELD OF THE INVENTION

The present disclosure related to a method for screening compounds having the ability to prevent, treat or reduce malodor development on body surfaces. In particular, the method screens for compounds having the ability of preventing sweat malodor development caused by malodor causing volatile acid compounds and/or malodor causing volatile sulphur compounds. The present disclosure is based on a sensitive analytical method to determine the presence of the precursors of malodor causing volatile acid compounds and/or malodor causing volatile sulphur compounds present in sweat, which are metabolised by bacteria, such as, for example, *Cornebacteria* or *Staphylococci* to malodor causing volatile acid compounds and malodor causing volatile sulphur compounds.

BACKGROUND

The prevention of axillary malodor is a constant objective of scientific endeavour. Sweat, secreted from apocrine sweat glands is odourless. However, axillary malodor develops as a result of the metabolic activity of certain strains of bacteria that have evolved to live in the axilla, and which are well adapted to growing on the peculiar cocktail of odourless precursors found in apocrine sweat.

An analytical method to determine the presence of the precursors of malodor causing volatile acid compounds and/or malodor causing volatile sulphur compounds present in sweat may then be used to more effectively combat axillary malodor development in subjects, for example by providing effective screening methods for compounds inhibiting the formation of malodor causing volatile acid compounds and/or malodor causing volatile sulphur compounds.

SUMMARY

A method,
wherein the method identifies compounds having the ability to prevent, treat, or reduce malodor development on body surfaces, the method comprising the steps of:
  a. contacting a subject with a test compound;
  b. collecting a sample comprising at least one malodor causing volatile compound from the headspace of the axilla of a subject;
  c. adsorbing the collected sample onto an adsorbent material; and
  d. determining, in the adsorbed collected sample, the amount of at least one malodor causing volatile compound selected from the group consisting of: 3-methyl-2-hexenoic acid (3M2H), 3-hydroxy-3-methylhexanoic acid (HMHA), and 3-methyl-3-sulfanylhexan-1-ol (MSH),
wherein the determining step is performed by thermal desorption GC/MS, and
wherein the test compound prevents, treats, or reduces malodor development on body surfaces if the amount of the at least one malodor causing volatile compound is lower, compared an amount of the amount of the at least one malodor causing volatile compound in a sample collected from a non-treated subject.

A method,
wherein the method identifies compounds having the ability to prevent, treat, or reduce malodor development on body surfaces, the method comprising the steps of:
  a. contacting a subject with a test compound;
  b. collecting a sample comprising at least one malodor causing volatile acid compound from a sample of clothing obtained from a subject;
  c. extracting the at least one malodor causing volatile acid compound from the collected sample of the subject's clothing with a solvent;
  d. forming an ester of the at least one malodor causing volatile acid compound;
  e. extracting the ester of the at least one malodor causing volatile acid compound, thereby forming an extracted sample, and
  f. determining, in the extracted sample, the amount of at least one ester of the malodor causing volatile acid compound selected from the group consisting of: 3-methyl-2-hexenoic acid (3M2H), and 3-hydroxy-3-methylhexanoic acid (HMHA),
wherein the determining step is performed by GC-MS/MS, and
wherein the test compound prevents, treats, or reduces malodor development on body surfaces if the amount of the extracted ester of the at least one malodor causing volatile acid compound is lower, compared an amount of the amount of the extracted ester of the at least one malodor causing volatile acid compound in a sample collected from a non-treated subject.

DETAILED DESCRIPTION

In the following description, reference is made to specific embodiments which may be practiced, which is shown by way of illustration. These embodiments are described in detail to enable those skilled in the art to practice the invention described herein, and it is to be understood that other embodiments may be utilized and that logical changes may be made without departing from the scope of the aspects presented herein. The following description of example embodiments is, therefore, not to be taken in a limited sense, and the scope of the various aspects presented herein is defined by the appended claims.

The Abstract is provided to comply with 37 C.F.R. § 1.72(b) to allow the reader to quickly ascertain the nature and gist of the technical disclosure. The Abstract is submitted with the understanding that it will not be used to interpret or limit the scope or meaning of the claims.

Figure 1:
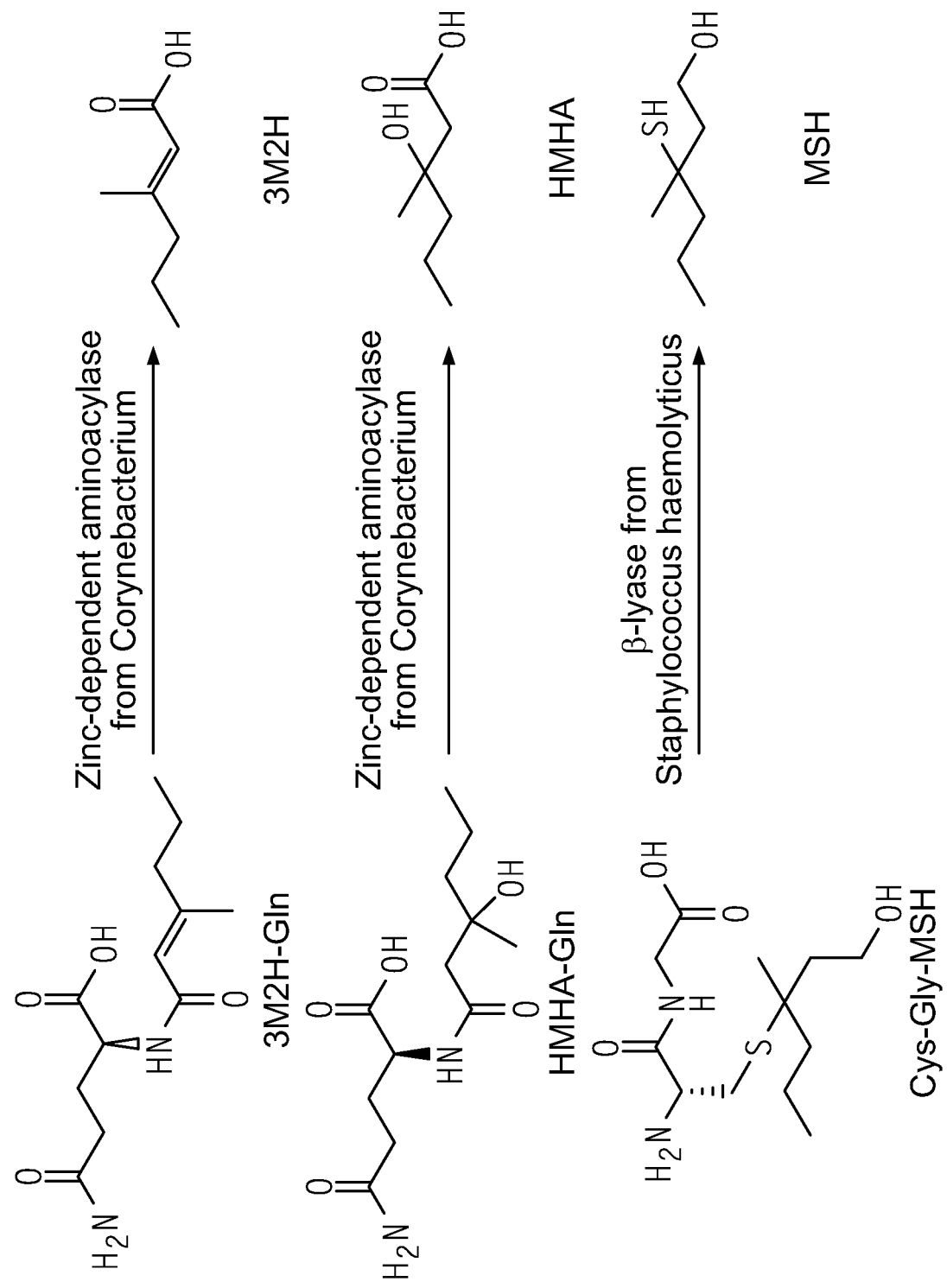
FIG. 1 shows a representation of the formation of the malodor causing volatile compounds 3-methyl-2-hexenoic acid (3M2H), 3-hydroxy-3-methylhexanoic acid (HMHA), and 3-methyl-3-sulfanylhexan-1-ol (MSH) from their respective precursors by the action of a zinc-dependent aminoacylase from *Corynebacteria* or a β-lyase from *Staphylococci*, according to some aspects presented herein.

Detection Methods According to Some Aspects Presented Herein:

Referring to FIG. 1, sweat contains certain odorless precursor compounds comprising conjugates of glutamine, or, in the case of 3-methyl-3-sulfanylhexan-1-ol, a cysteinylglycine-S-conjugate of 3-methyl-3-sulfanylhexan-1-ol. Bacteria, such as, for example, *Corynebacteria* or *Staphylococci*, present on the surface of the subject's skin metabolize the odorless precursor compounds to 3-methyl-2-hexenoic acid (3M2H), 3-hydroxy-3-methylhexanoic acid (HMHA), and 3-methyl-3-sulfanylhexan-1-ol (MSH), resulting in the formation of malodor. The metabolism is catalysed by a zinc-dependent aminoacylase from *Corynebacteria* or a β-lyase from *Staphylococci*.

Without intending to be limited to any particular theory, the odor detection threshold of 3M2H and HMHA is low (3M2H: volatility—40 μg/L, ODT—1.44 to $2.59 \times 10^{-4}$ μg/L; HMHA: volatility—0.29 μg/L, ODT—1.49 to $2.00 \times 10^{-4}$ μg/L). Consequently, a subject may perceive an intense malodor, even when either 3M2H, or HMHA, are only be present in small amounts.

Figure 2:
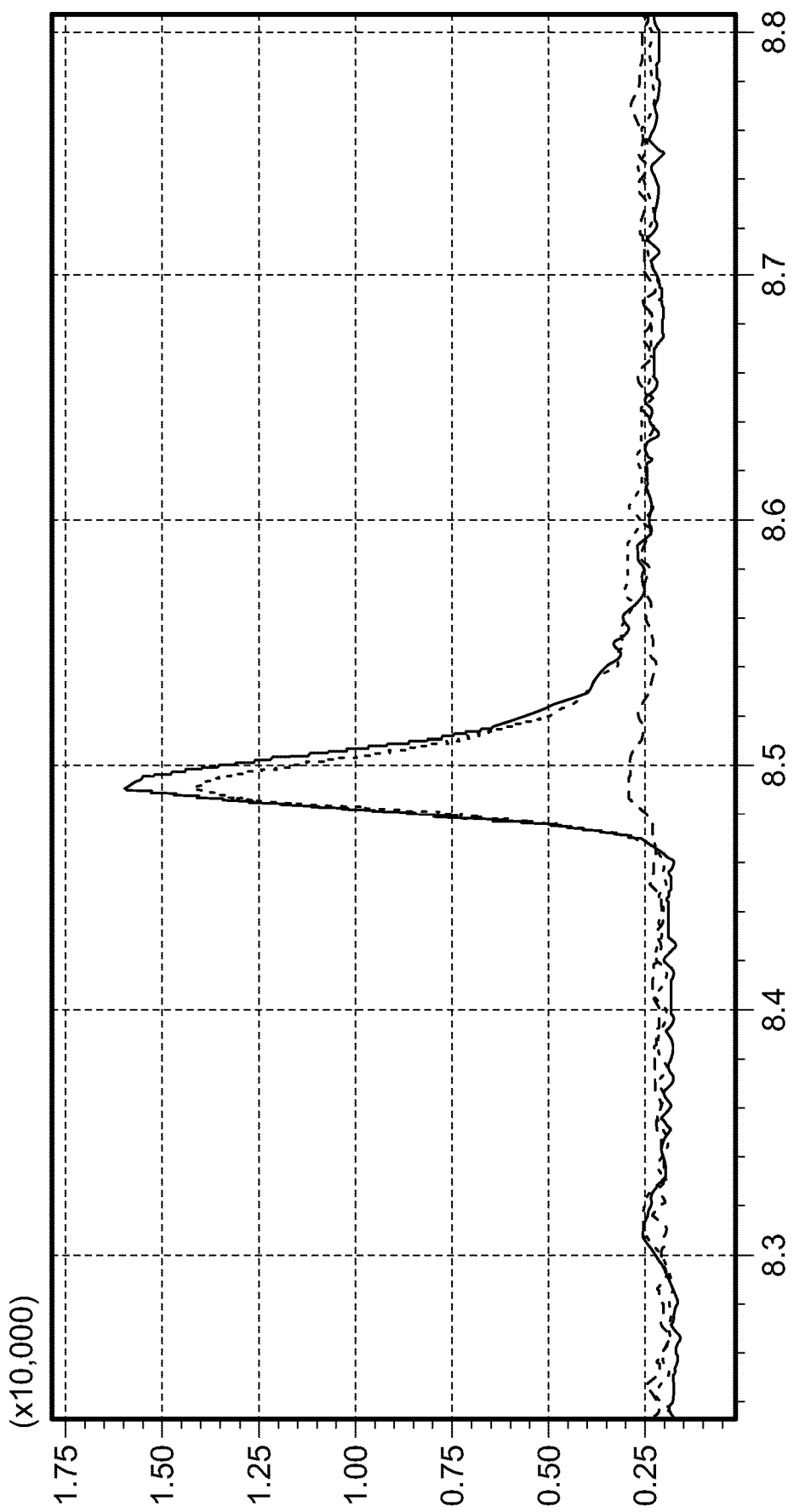
FIG. 2 shows three replicate GC-MS/MS chromatographs of 3M2H samples obtained using conventional methods.

Without intending to be limited to any particular theory, an analytical method to determine the presence of the precursors of malodor causing volatile acid compounds present in sweat may be used to more effectively combat axillary malodor development in subjects, for example by providing effective screening methods for compounds inhibiting the formation of malodor causing volatile acid compounds. Referring to FIG. 2, the reproducibility and/or sensitivity of existing methods for the detection of 3-methyl-2-hexenoic acid (3M2H), 3-hydroxy-3-methylhexanoic acid (HMHA) and 3-methyl-3-sulfanylhexan-1-ol (MSH) are low. Factors contributing to the poor reproducibility and/or sensitivity include, but are not limited to the adsorption of the malodor causing volatile acid compounds onto the detection apparatus, the small amounts present in sweat, and the like. FIG. 2 shows the poor reproducibility of conventional methods, possibly the result of adsorption of the sample to the metal surfaces of the instrumentation.

The present disclosure provides analytical methods that increase the sensitivity of methods for the detection of 3-methyl-2-hexenoic acid (3M2H), 3-hydroxy-3-methylhexanoic acid (HMHA), and 3-methyl-3-sulfanylhexan-1-ol (MSH), by reducing the adsorption of the malodor causing volatile compounds onto the detection apparatus. The present disclosure provides two methods that directly detect and quantify malodor causing volatile compounds. As used herein, the term "malodor causing volatile compounds" includes the acids 3-methyl-2-hexenoic acid (3M2H), 3-hydroxy-3-methylhexanoic acid (HMHA) (referred to herein as "malodor causing volatile acid compounds"), and 3-methyl-3-sulfanylhexan-1-ol (MSH) (referred to herein as "malodor causing volatile sulphur compound(s)").

In one aspect, the present disclosure provides a method that directly detects and quantifies volatile malodor causing volatile compounds from the headspace of a subject's axilla, via thermal desorption GC-MS with selected ion monitoring (SIM) mode. In an alternate aspect, the present disclosure provides a method that directly detects and quantifies volatile malodor causing volatile acid compounds from an item of the subject's clothing, or a cotton swab, or other absorbent material utilized to collect a sample of sweat from the subject, wherein the volatile malodor causing volatile acid compounds are enriched, derivatized, and quantified by GC-MS/MS.

In some aspects, the methods presented herein are capable of detecting the at least one malodor causing volatile compound at a concentration ranging from 0.5 to 100 ng. In some aspects, the methods presented herein are capable of detecting the at least one malodor causing volatile compound at a concentration ranging from 0.5 to 90 ng. In some aspects, the methods presented herein are capable of detecting the at least one malodor causing volatile compound at a concentration ranging from 0.5 to 80 ng. In some aspects, the methods presented herein are capable of detecting the at least one malodor causing volatile compound at a concentration ranging from 0.5 to 70 ng. In some aspects, the methods presented herein are capable of detecting the at least one malodor causing volatile compound at a concentration ranging from 0.5 to 60 ng. In some aspects, the methods presented herein are capable of detecting the at least one malodor causing volatile compound at a concentration ranging from 0.5 to 50 ng. In some aspects, the methods presented herein are capable of detecting the at least one malodor causing volatile compound at a concentration ranging from 0.5 to 40 ng. In some aspects, the methods presented herein are capable of detecting the at least one malodor causing volatile compound at a concentration ranging from 0.5 to 30 ng. In some aspects, the methods presented herein are capable of detecting the at least one malodor causing volatile compound at a concentration ranging from 0.5 to 20 ng. In some aspects, the methods presented herein are capable of detecting the at least one malodor causing volatile compound at a concentration ranging from 0.5 to 10 ng. In some aspects, the methods presented herein are capable of detecting the at least one malodor causing volatile compound at a concentration ranging from 0.5 to 9 ng. In some aspects, the methods presented herein are capable of detecting the at least one malodor causing volatile compound at a concentration ranging from 0.5 to 8 ng. In some aspects, the methods presented herein are capable of detecting the at least one malodor causing volatile compound at a concentration ranging from 0.5 to 7 ng. In some aspects, the methods presented herein are capable of detecting the at least one malodor causing volatile compound at a concentration ranging from 0.5 to 6 ng. In some aspects, the methods presented herein are capable of detecting the at least one malodor causing volatile compound at a concentration ranging from 0.5 to 5 ng. In some aspects, the methods presented herein are capable of detecting the at least one malodor causing volatile compound at a concentration ranging from 0.5 to 4 ng. In some aspects, the methods presented herein are capable of detecting the at least one malodor causing volatile compound at a concentration ranging from 0.5 to 3 ng. In some aspects, the methods presented herein are capable of detecting the at least one malodor causing volatile compound at a concentration ranging from 0.5 to 2 ng. In some aspects, the methods presented herein are capable of detecting the at least one malodor causing volatile compound at a concentration ranging from 0.5 to 1 ng.

In some aspects, the methods presented herein are capable of detecting the at least one malodor causing volatile acid compound at a concentration ranging from 0.01 to 5 µg/ml. In some aspects, the methods presented herein are capable of detecting the at least one malodor causing volatile acid compound at a concentration ranging from 0.01 to 4 µg/ml. In some aspects, the methods presented herein are capable of detecting the at least one malodor causing volatile acid compound at a concentration ranging from 0.01 to 3 µg/ml. In some aspects, the methods presented herein are capable of detecting the at least one malodor causing volatile acid compound at a concentration ranging from 0.01 to 2 µg/ml. In some aspects, the methods presented herein are capable of detecting the at least one malodor causing volatile acid compound at a concentration ranging from 0.01 to 1 µg/ml. In some aspects, the methods presented herein are capable of detecting the at least one malodor causing volatile acid compound at a concentration ranging from 0.01 to 0.9 µg/ml. In some aspects, the methods presented herein are capable of detecting the at least one malodor causing volatile acid compound at a concentration ranging from 0.01 to 0.8 µg/ml. In some aspects, the methods presented herein are capable of detecting the at least one malodor causing volatile acid compound at a concentration ranging from 0.01 to 0.7 µg/ml. In some aspects, the methods presented herein are capable of detecting the at least one malodor causing volatile acid compound at a concentration ranging from 0.01 to 0.6 µg/ml. In some aspects, the methods presented herein are capable of detecting the at least one malodor causing volatile acid compound at a concentration ranging from 0.01 to 0.5 µg/ml. In some aspects, the methods presented herein are capable of detecting the at least one malodor causing volatile acid compound at a concentration ranging from 0.01 to 0.4 µg/ml. In some aspects, the methods presented herein are capable of detecting the at least one malodor causing volatile acid compound at a concentration ranging from 0.01 to 0.3 µg/ml. In some aspects, the methods presented herein are capable of detecting the at least one malodor causing volatile acid compound at a concentration ranging from 0.01 to 0.2 µg/ml. In some aspects, the methods presented herein are capable of detecting the at least one malodor causing volatile acid compound at a concentration ranging from 0.01 to 0.1 µg/ml. In some aspects, the methods presented herein are capable of detecting the at least one malodor causing volatile acid compound at a concentration ranging from 0.01 to 0.09 µg/ml. In some aspects, the methods presented herein are capable of detecting the at least one malodor causing volatile acid compound at a concentration ranging from 0.01 to 0.08 µg/ml. In some aspects, the methods presented herein are capable of detecting the at least one malodor causing volatile acid compound at a concentration ranging from 0.01 to 0.07 µg/ml. In some aspects, the methods presented herein are capable of detecting the at least one malodor causing volatile acid compound at a concentration ranging from 0.01 to 0.06 µg/ml. In some aspects, the methods presented herein are capable of detecting the at least one malodor causing volatile acid compound at a concentration ranging from 0.01 to 0.05 µg/ml. In some aspects, the methods presented herein are capable of detecting the at least one malodor causing volatile acid compound at a concentration ranging from 0.01 to 0.04 µg/ml. In some aspects, the methods presented herein are capable of detecting the at least one malodor causing volatile acid compound at a concentration ranging from 0.01 to 0.03 µg/ml. In some aspects, the methods presented herein are capable of detecting the at least one malodor causing volatile acid compound at a concentration ranging from 0.01 to 0.02 µg/ml.

In some aspects, the at least one malodor causing volatile compound is selected from the group consisting of: 3-methyl-2-hexenoic acid (3M2H), 3-hydroxy-3-methylhexanoic acid (HMHA), and 3-methyl-3-sulfanylhexan-1-ol (MSH).

Other malodor causing volatile compounds suitable for detection by methods presented herein include: C6-C11 fatty acids, (Z)-3-methyl-2-hexenoic acid (Z3M2H), the malodor causing volatile acid compounds disclosed in U.S. Pat. No. 9,101,783, and the malodor causing volatile acid compounds disclosed in International Patent Application Publication No/WO 2006/079934 A1.

In some aspects, the malodor causing volatile acid compound is 3M2H.

In some aspects, the malodor causing volatile acid compound is HMHA.

In some aspects, the malodor causing volatile sulphur compound is MSH.

Detection Methods: Referring to Example 1, and FIGS. 3 and 4, in some aspects, the present disclosure provides a method,
  wherein the method detects at least one malodor causing volatile compound in a sample obtained from a subject,
  wherein the method comprises the steps of:
    a. collecting a sample comprising the at least one malodor causing volatile compound from the headspace of the axilla of the subject;
    b. adsorbing the collected sample onto an adsorbent material; and
    c. determining, in the adsorbed collected sample, the amount of at least one malodor causing volatile compound selected from the group consisting of: 3-methyl-2-hexenoic acid (3M2H), 3-hydroxy-3-methylhexanoic acid (HMHA), and 3-methyl-3-sulfanylhexan-1-ol (MSH),
  wherein the determining step is performed by thermal desorption GC/MS.

Figure 3:
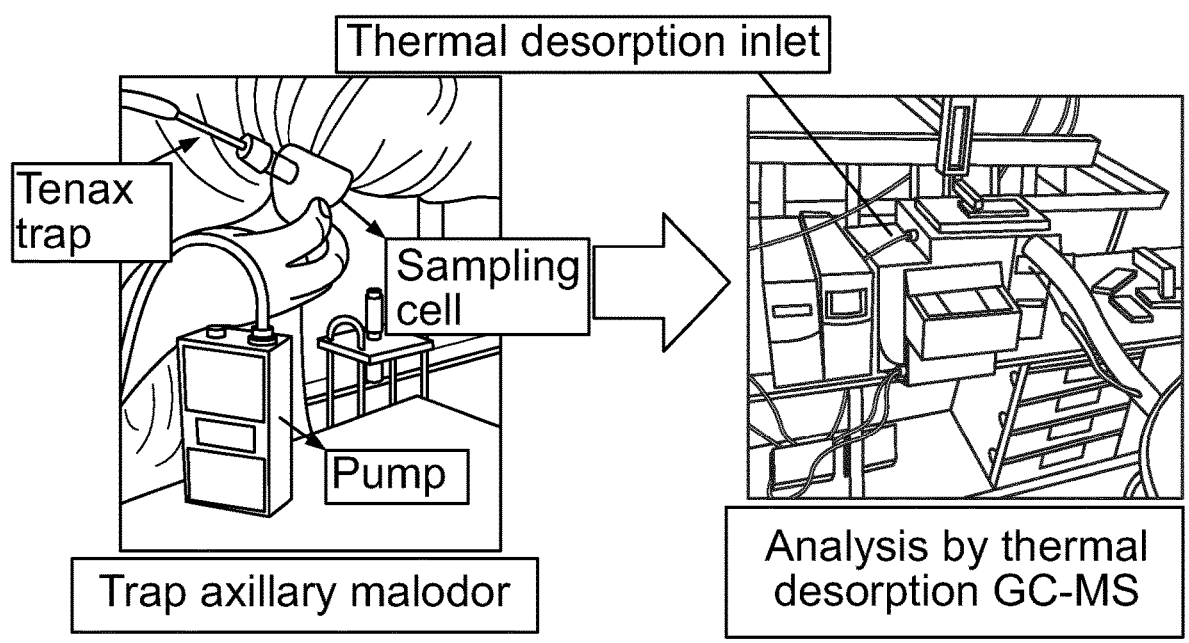
FIG. 3 shows a detection apparatus according to some aspects presented herein. In the some embodiments, unlike the depiction in the figure, the sampling cell directly contacts with the skin, without the shirt.

Referring to FIG. 3, in some aspects, the sample comprising the at least one malodor causing volatile compound is collected using a sampling apparatus comprising a sampling cell, having an open end, a sampling tube containing an adsorbent resin that is fluidly connected to the sampling cell and the end distal to the open end, and a pump, configured to draw air through the sampling cell and sampling tube. During collection, the subject places the sampling cell under their axilla, with the open end of the sampling cell is tightly contacted to the skin surface of the subject.

In some aspects, the air is drawn through the sampling cell and sampling tube for up to 60 minutes.

In some aspects, the air is drawn through the sampling cell and sampling tube for between 15 to 60 min.

In some aspects, the air is drawn through the sampling cell and sampling tube for 60 min. In some aspects, the air is drawn through the sampling cell and sampling tube for 50 min. In some aspects, the air is drawn through the sampling cell and sampling tube for 40 min. In some aspects, the air is drawn through the sampling cell and sampling tube for 30 min. In some aspects, the air is drawn through the sampling cell and sampling tube for 20 min. In some aspects, the air is drawn through the sampling cell and sampling tube for 10 min.

In some aspects, the air is drawn through the sampling cell and sampling tube at a rate from 100 to 200 mL/min. In some aspects, the air is drawn through the sampling cell and sampling tube at a rate of 150 mL/min.

In some aspects, the collection step is repeated. The step may be repeated on the same axilla, or, alternative, on the subject's other axilla.

In some aspects, the surfaces of the sampling cell and/or the sampling tube are treated with an agent that prevents, reduces, or inhibits the adsorption of the least one malodor causing volatile acid compound to the surface of the sampling cell and/or the sampling tube. In some aspects, the treatment comprises contacting the surfaces with a 5% v/v solution of dichlorodimethylsilane (DMDCS) in toluene, for 15 min, followed by at least one rinse with toluene.

In some aspects, the adsorbent material comprises a material configured to trap volatile compounds, such as, for example, an adsorbent resin, glass wool, glass beads, and the like.

In some aspects, the adsorbent material comprises an adsorbent resin, selected from the group consisting of: the adsorbent resin sold under the trade name TENAX TA, the adsorbent resin sold under the trade name TENAX GR, the adsorbent resin sold under the trade name CARBOTRAP, the adsorbent resin sold under the trade name CARBOTRAP C, the adsorbent resin sold under the trade name CARBOSIEVE SIII, and the adsorbent resin sold under the trade name CARBOXEN 569.

In some aspects, the adsorbent material is the adsorbent resin sold under the trade name TENAX TA.

In some aspects, the adsorbent material is pre-treated. The pre-treatment may increase the sensitivity of the detection method. In some aspects, the pre-treatment may reduce, prevent, or decrease the adsorption of the at least one malodor causing volatile compound to the surfaces of the sampling cell and/or the sampling tube.

In some aspects, the pre-treatment comprises a first treatment with an agent that prevents, reduces, or inhibits the adsorption of the least one malodor causing volatile acid compound to the surface of the sampling cell and/or the sampling tube, followed by a second treatment. In some aspects, the first treatment comprises contacting the adsorbent material with a 5% v/v solution of dichlorodimethylsilane (DMDCS) in toluene, for 15 min, followed by at least one rinse with toluene.

In some aspects, the adsorbent material is dried following the first treatment, using an in inert gas, such as, for example, $N_2$. In some aspects, the second treatment comprises treatment of the dried adsorbent material with acetone, followed by a drying step, using an inert gas.

In some aspects, the adsorbent material is pre-treated with acetone, followed by a drying step, using an inert gas, such as, for example, $N_2$.

The sampling cell may be made from any material readily selectable by one of ordinary skill in the art, such as, for example, glass, stainless steel, and the like.

Figure 4:
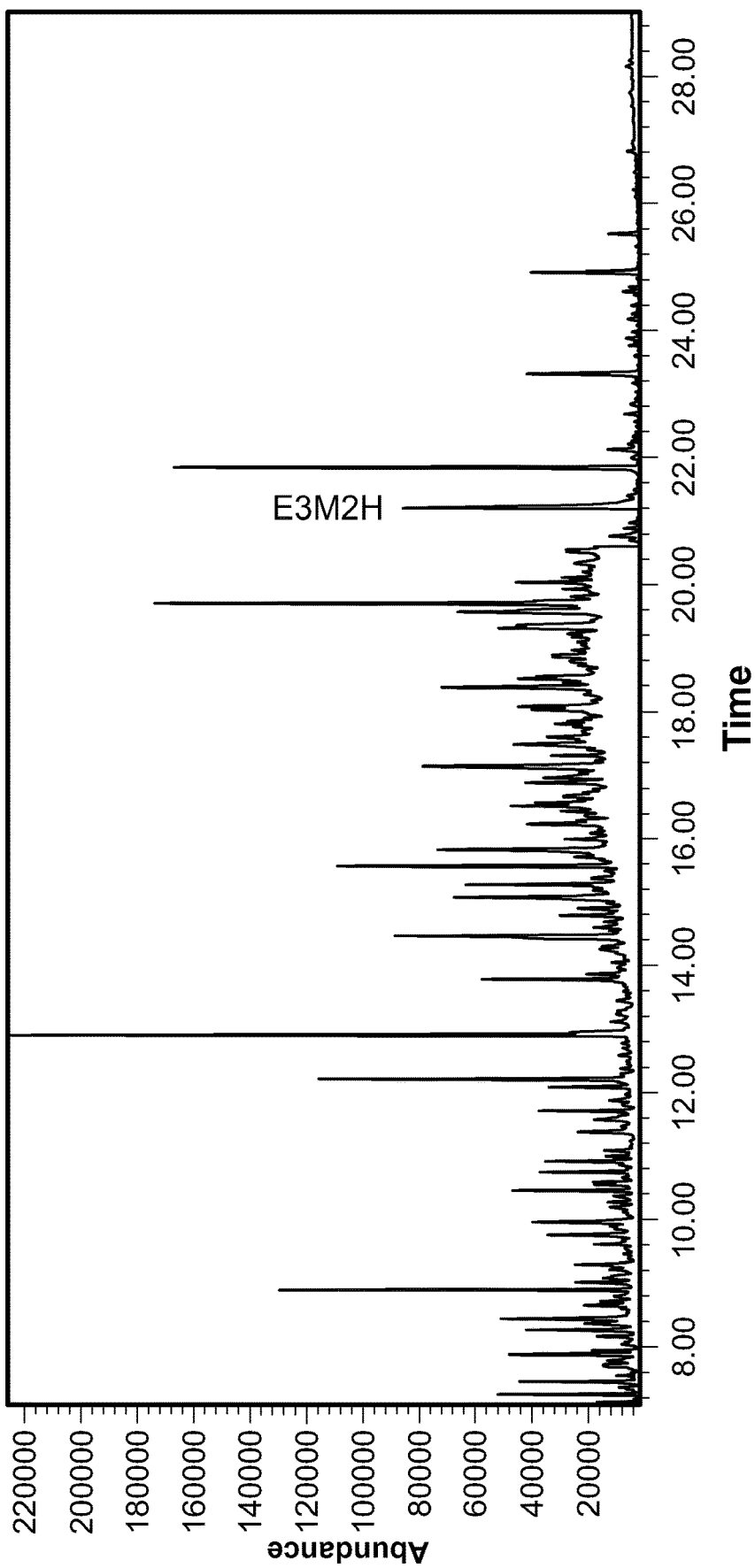
FIG. 4 shows a representative chromatogram obtained according to the methods presented herein.

In some aspects, the determining step is performed by thermal desorption GC/MS, wherein the collected sample is passed over an analytical column, and the at least one malodor causing volatile acid compound is quantified via selected ion monitoring (SIM) mode. In some aspects, the collected sample is passed over a DB-wax column. Alternatively, the collected sample is passed over a DB-1, DB-5, DB-17 DB-23, or a DB-FFAP column. A representative chromatograph is shown in FIG. 4.

Figure 5:
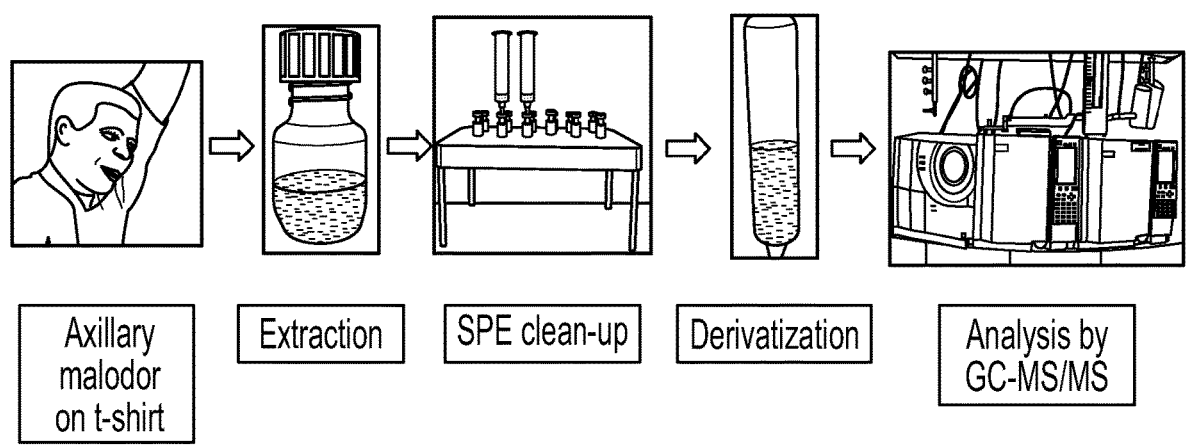
FIG. 5 shows a detection apparatus and method according to some aspects presented herein.

Referring to Example 2, and FIG. 5, in some aspects, the present disclosure provides a method, wherein the method detects at least one malodor causing volatile acid compound in a sample obtained from a subject, wherein the method comprises the steps of:
  a. collecting a sample comprising at least one malodor causing volatile acid compound from a sample of clothing obtained from a subject;
  b. extracting the at least one malodor causing volatile acid compound from the collected sample of the subject's clothing with a solvent;
  c. forming an ester of the at least one malodor causing volatile acid compound;
  d. extracting the ester of the at least one malodor causing volatile acid compound, thereby forming an extracted sample,
  e. determining, in the extracted sample, the amount of at least one ester of the malodor causing volatile acid compound selected from the group consisting of: 3-methyl-2-hexenoic acid (3M2H), and 3-hydroxy-3-methylhexanoic acid (HMHA), wherein the determining step is performed by GC-MS/MS.

Referring to FIG. 5, in some aspects, extraction of the at least one malodor causing volatile acid compound from the subject's clothing is achieved by a method comprising the steps of:
  a. collecting an under-arm portion of an item of clothing worn by the subject; and
  b. sonicating the collected portion of clothing in a solvent, thereby obtaining the extracted at least one malodor causing volatile acid compound.

In some aspects, the at least one malodor causing volatile acid compound is extracted from an adsorbent pad, such as, for example, a cotton swab, and the like, by a method comprising the steps of:
  a. applying the adsorbent pad to an area of the subject's skin for a time sufficient to collect a sample of the subject's sweat; and
  b. sonicating the adsorbent pad containing the sample of the subject's sweat in a solvent, thereby obtaining the extracted at least one malodor causing volatile acid compound.

In some aspects, the solvent is a 5% v/v ethanol solution in water.

In some aspects, the pH of the extracted at least one malodor causing volatile acid compound is adjusted to ensure the at least one malodor causing volatile acid compound is an anion. In some aspects, the pH ranges from pH 5.6 to pH 9.

In some aspects, the extracted at least one malodor causing volatile acid compound is further treated with a buffer, to adjust the pH of the extracted at least one malodor causing volatile acid compound to pH 7. In some aspects, the buffer is 50 mM sodium acetate.

In some aspects, the extracted at least one malodor causing volatile acid compound is applied to an anion exchange resin. In some aspects, the anion exchange resin is pre-conditioned, prior to the application of the extracted at least one malodor causing volatile acid compound.

In some aspects, the pre-conditioning comprises treatment with methanol, followed by ethanol.

In some aspects, anion exchange resin is selected from the group consisting of: the anion exchange resin sold under the trade name SPE, the anion exchange resin sold under the trade name SAMPLIQ SAX, the anion exchange resin sold under the trade name PHENOMENEX STRATA-X-A, the anion exchange resin sold under the trade name Agilent SAMPLIQ SAX, and the anion exchange resin sold under the trade name HYPERSEP SAX.

In some aspects, the anion exchange resin may be any anion exchange resin with similar anion exchange groups as the anion exchange resin sold under the trade name SPE.

In some aspects, the extracted at least one malodor causing volatile acid compound may be converted to methyl, ethyl, propyl, or butyl esters. In these aspects, the extracted at least one malodor causing volatile acid compound may be reacted with $BF_3$ and an alcohol selected from the group consisting of: methanol, ethanol, propanol, and butanol.

In some aspects, the reaction of the extracted at least one malodor causing volatile acid compound with $BF_3$/alcohol is achieved by a method, comprising the steps of:
  a. after the application of the extracted at least one malodor causing volatile acid compound is applied to an SPE cartridge, washing the cartridge with 2 mL 50 mM sodium acetate;
  b. eluting the applied extracted at least one malodor causing volatile acid compound with 6 mL alcohol, followed by 6 mL alcohol with 2% trifluoroacetic acid (TFA);
  c. collecting the eluate;
  d. treating the collected eluate with 2 mL boron trifluoride (14% w/w);
  e. incubating the treated eluate a 60° C. for 3 h with continuous stirring;
  f. cooling the incubated eluate to room temperature, and stopping the reaction by adding to the cooled eluate, 1 ml water; and
  g. neutralizing the TFA, and adjusting the pH of the incubated eluate to a pH ranging from pH 6 to pH 7, by adding 0.5M $NaHCO_3$.

In some aspects, the reaction of the extracted at least one malodor causing volatile acid compound with $BF_3$/methanol is achieved by a method, comprising the steps of:
  a. after the application of the extracted at least one malodor causing volatile acid compound is applied to an SPE cartridge, washing the cartridge with 2 mL 50 mM sodium acetate;
  b. eluting the applied extracted at least one malodor causing volatile acid compound with 6 mL MeOH, followed by 6 mL MeOH with 2% trifluoroacetic acid (TFA);
  c. collecting the eluate;
  d. treating the collected eluate with 2 mL boron trifluoride (14% w/w);
  e. incubating the treated eluate a 60° C. for 3 h with continuous stirring;
  f. cooling the incubated eluate to room temperature, and stopping the reaction by adding to the cooled eluate, 1 ml water; and
  g. neutralizing the TFA, and adjusting the pH of the incubated eluate to a pH ranging from pH 6 to pH 7, by adding 0.5M $NaHCO_3$.

In some aspects, the elution of the applied extracted at least one malodor causing volatile acid compound may be via ethanol or acetonitrile.

In some aspects, the the applied extracted at least one malodor causing volatile acid compound is eluted with a volume ranging from 3 to 9 mL.

In some aspects, the concentration of the TFA ranges from 1 to 5% v/v.

In some aspects, the collected eluate may be treated with formic acid or acetic acid.

In some aspects, the collected eluate with 1 to 5 mL boron trifluoride (14% w/w).

In some aspects, ester of the at least one malodor causing volatile acid compound is extracted by the addition of 2×10 ml $CH_2Cl_2$.

In some aspects the ester of the at least one malodor causing volatile acid compound is extracted by the addition of a solvent selected from the group consisting of pentane, heptane, and cyclohexane.

In some aspects, the incubation time is from 0.5 h to 5 h.

In some aspects, the extracted ester of the at least one malodor causing volatile acid compound is concentrated to a final volume of 5 mL, prior to analysis using GC-MS/MS.

In some aspects, the GC-MS/MS is under optimized MRM transitions.

In some aspects, the extracted ester of the at least one malodor causing volatile acid compound is concentrated under an inert gas, such as, for example, $N_2$.

Figure 6:
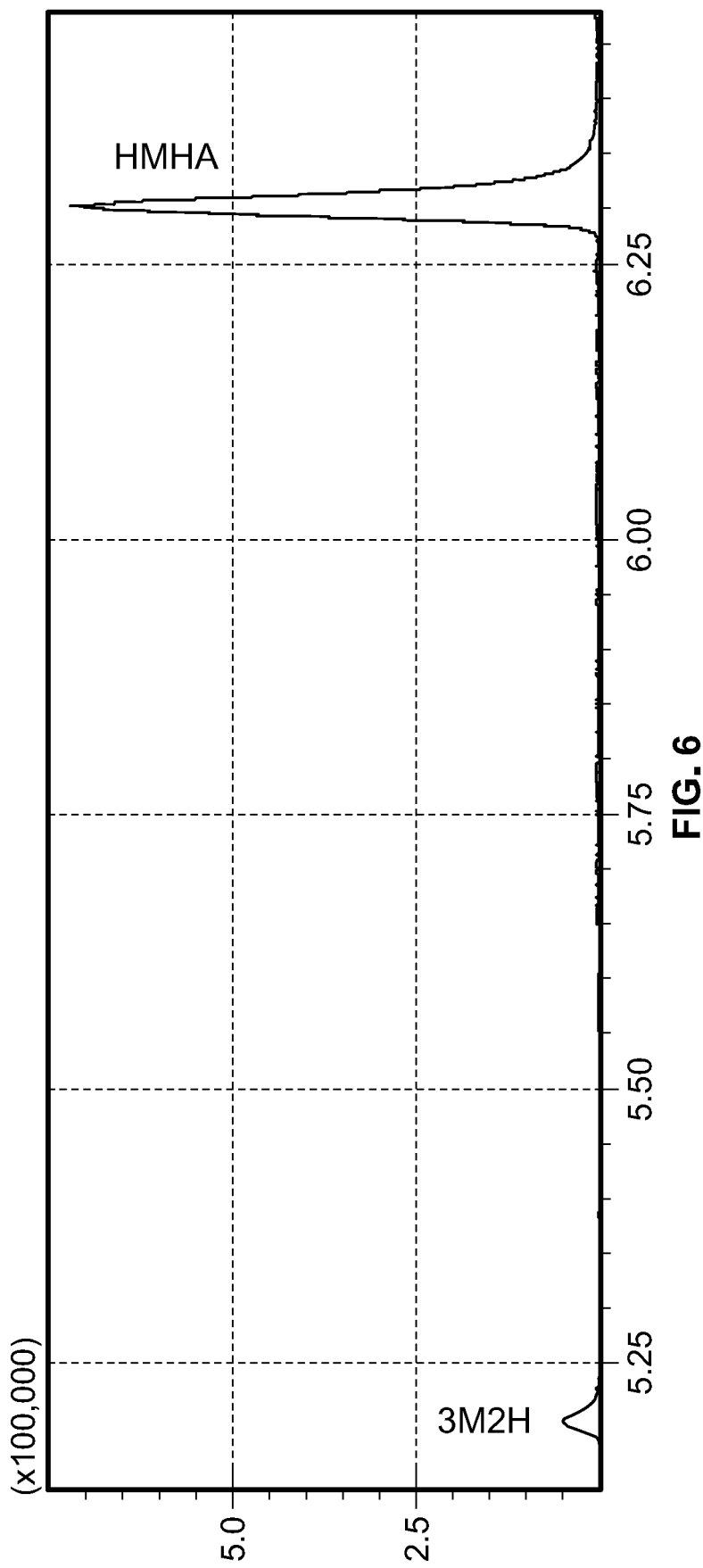
FIG. 6 shows a representative chromatogram obtained according to the methods presented herein.
Figure 7:
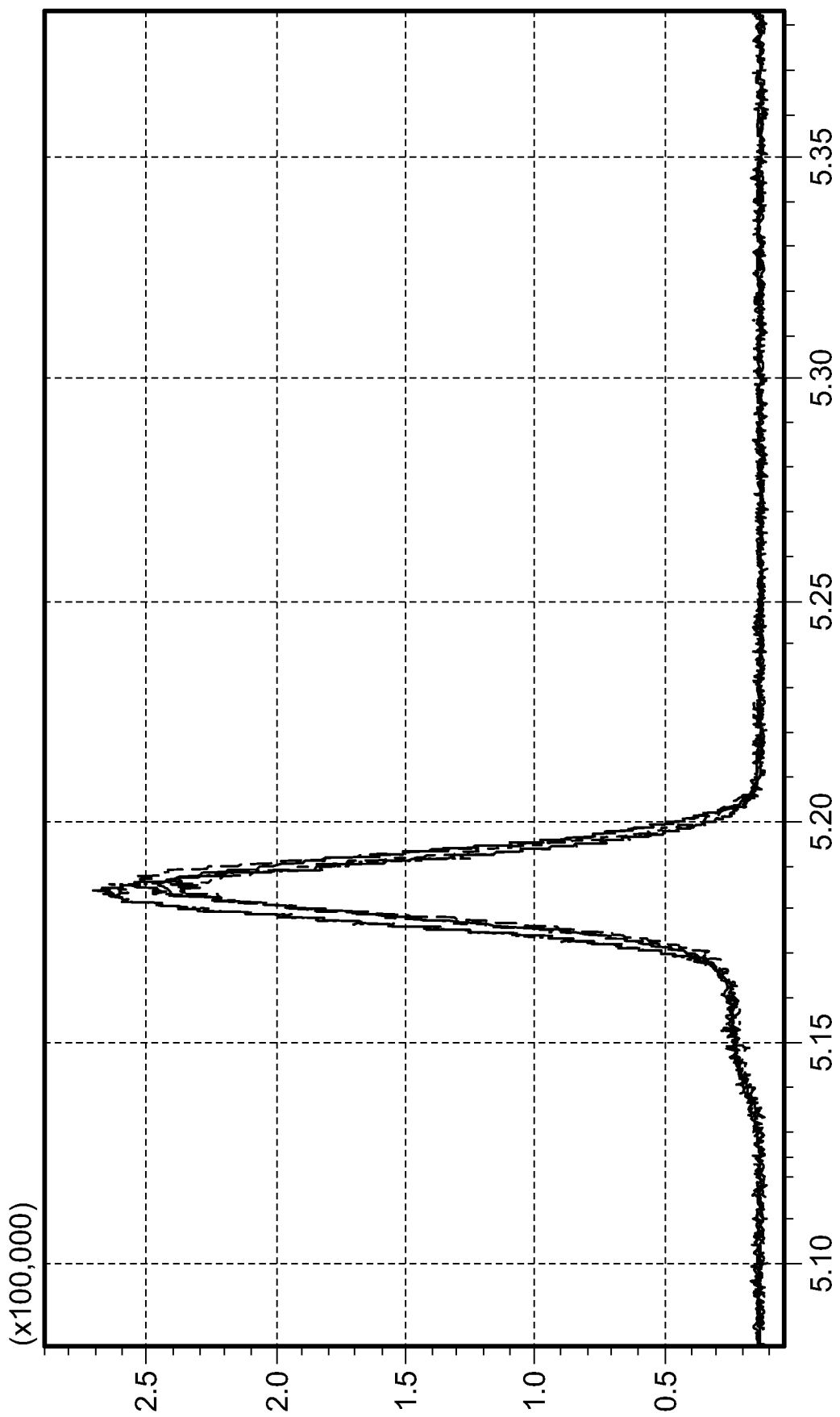
FIG. 7 shows a representative replicate chromatograms obtained according to the methods presented herein.

In some aspects, the determining step is performed GC/MS/MS, wherein the collected sample is passed over an analytical column, and the ester of the at least one malodor causing volatile acid compound is quantified via optimized MRM transitions. In some aspects, the collected sample is passed over a DB-wax column. Alternatively, the collected sample is passed over a DB-1, DB-5, DB-17, DB-23, or a DB-FFAP column. A representative chromatograph, obtained using synthetic body odor is shown in FIG. 6. Replicate chromatographs are shown in FIG. 7.

Screening Methods According to Some Aspects Presented Herein:

In some aspects, the present disclosure provides a method, wherein the method identifies compounds having the ability to prevent, treat, or reduce malodor development on body surfaces, the method comprising the steps of:
  a. contacting a subject with a test compound;
  b. collecting a sample comprising at least one malodor causing volatile compound from the headspace of the axilla of a subject;
  c. adsorbing the collected sample onto an adsorbent material; and
  d. determining, in the adsorbed collected sample, the amount of at least one malodor causing volatile compound selected from the group consisting of: 3-methyl-2-hexenoic acid (3M2H), 3-hydroxy-3-methylhexanoic acid (HMHA), and 3-methyl-3-sulfanylhexan-1-ol (MSH),
wherein the determining step is performed by thermal desorption GC/MS, and
wherein the test compound prevents, treats, or reduces malodor development on body surfaces if the amount of the at least one malodor causing volatile compound is lower, compared an amount of the amount of the at least one malodor causing volatile compound in a sample collected from a non-treated subject.

In some aspects, the present disclosure provides a method, wherein the method identifies compounds having the ability to prevent, treat, or reduce malodor development on body surfaces, the method comprising the steps of:
  a. contacting a subject with a test compound;
  b. collecting a sample comprising at least one malodor causing volatile acid compound from a sample of clothing obtained from a subject;
  c. extracting the at least one malodor causing volatile acid compound from the collected sample of the subject's clothing with a solvent;
  d. forming an ester of the at least one malodor causing volatile acid compound;

e. extracting the ester of the at least one malodor causing volatile acid compound, thereby forming an extracted sample, and f. determining, in the extracted sample, the amount of at least one ester of the malodor causing volatile acid compound selected from the group consisting of: 3-methyl-2-hexenoic acid (3M2H), and 3-hydroxy-3-methylhexanoic acid (HMHA), wherein the determining step is performed by GC-MS/MS, and wherein the test compound prevents, treats, or reduces malodor development on body surfaces if the amount of the extracted ester of the at least one malodor causing volatile acid compound is lower, compared an amount of the amount of the extracted ester of the at least one malodor causing volatile acid compound in a sample collected from a non-treated subject.

In some aspects, the test compounds may be the test compounds disclosed in U.S. Pat. No. 9,101,783.

In some aspects, the test compounds may be the test compounds disclosed in International Patent Application Publication No. WO 2006/079934 A1.

The present invention is best illustrated but is not limited to the following examples.

EXAMPLES

Example 1

Quantification of Malodor Causing Volatile Compounds from an Individual Subject

Deactivation of the Sampling Tube and Sampling Cell: The sampling tube, and glass wool were soaked in a 5% (v/v) dichlorodimethylsilane (DMDCS) in toluene solution for 15 min, and then rinsed twice with toluene. The rinsed items were then soaked in methanol for 15 min, and rinsed twice with methanol, then dried with $N_2$. The adsorbent material, such as TENAX was then rinsed with acetone and dried with high-purity N2.

Malodor causing volatile compounds were collected using the headspace sampling cell (FIG. 3). Referring to FIG. 3, one side of the headspace sampling cell was connected with Tenax trap which was pumped by a vacuum pump. The subject held the sampling cell tightly under one axilla and pumped at 150 mL/min air flow rate for 20 min from one side, and then also pumped for 20 mins again from the other axilla.

Thermal desorption GC/MS was performed on 7890A/5975C (Agilent) equipped with the OPTIC 4 thermal desorption module. The desorbed compounds were cryofocused in the OPTIC 4 at −50° C. After desorption, OPTIC 4 was programmed from −50° C. to 250° C. (held for 400 sec) at 60° C./s to inject the trapped compounds into a DB-WAX column (30 m×0.25 mm i.d.×0.25 μm film thickness, J & W Scientific, Agilent Technologies, Foster City, CA). The DB-WAX column used the following temperature program: 50° C. (held for 7 min), 50° C.-250° C. (10° C./min, held for 2 min). The ion source temperature of the mass spectrometer was 230° C. and transfer line temperature was set at 250° C. Helium was used as carrier gas at constant flow rate 1 mL/min and split flow was set as 10 mL/min.

Calibration Curves, LOD, LOQ and Reproducibility: The malodor causing volatile acid compounds in the adsorbed sample were analyzed by thermal desorption GC/MS with selected fragment ions 100, 113 and 128 for E3M2H. E3M2H was quantified using the area of the selected ion 100 with external standard curve, which composed of a series of 0.5, 1, 2, 5, 10, 20, 30 and 50 ng samples. The standard curves are as follows y=126903x−140318 with $R^2$=0.9963. The analytical method had a high sensitivity, with LOD and LOQ of 0.2 ng and 0.5 ng respectively (Table 1). The reproducibility of the method was evaluated by quantification of E3M2H released from its standard solution. E3M2H emanated from its standard solution and 1:1 diluted E3M2H standard solution sample was separately quantified as 26.5±3.7 ng (n=6) and 11.2±3.6 ng (n=6) (Table 1).

TABLE 1

LOD, LOQ, dynamic ranges and reproducibility of released E3M2H analyzed by headspace GC-MS

|  | LOD | LOQ | Dynamic ranges | E3M2H standard solution | 1:1 diluted E3M2H standard solution |
|---|---|---|---|---|---|
| E3M2H (ng) | 0.2 | 0.5 | 0.5–50 | 26.5 ± 3.7 (n = 6) | 11.2 ± 3.6 (n = 6) |

Released E3M2H from 9 Caucasian subjects were trapped by headspace sampling and analyzed by thermal desorption GC-MS with SIM mode. The chromatogram of the axillary malodor causing volatile acid compounds released by the subject is shown in FIG. 4. Released E3M2H was detected in 6 subjects, except subject 6 and subject 8 (Table 2). Released E3M2H in six detected subjects ranged from 0.72 ng to 30.52 ng.

TABLE 2

Quantities of E3M2H released from the subjects (ng)

| Subjects | Gender | Released E3M2H (ng) |
|---|---|---|
| 1 | Female | 2.56 |
| 2 | Male | 0.72 |
| 3 | Female | 1.16 |
| 4 | Male | 20.07 |
| 5 | Female | 1.75 |
| 6 | Male | ND |
| 7 | Female | 30.52 |
| 8 | Male | ND |
| 9 | Female | 3.52 |

Example 2

Quantification of Malodor Causing Volatile Acid Compounds from an Individual Subject's Clothing Subjects wore a washed white cotton T-shirt for 24 h and were asked to use a specific shower-gel and non-antimicrobial roll-on products before the day of wearing T-Shirt. One approximately 10 cm long×10 cm wide underarm area was cut from the worn T-shirt, and then sonicated in 20 mL 5% EtOH for 30 min.

The extraction was adjusted to pH 7 with 50 mM sodium acetate before loading on to an SPE cartridge (6 cc/500 mg, Oasis MAX cartridge, Waters, MA). The cartridge was conditioned with 10 mL MeOH and 15 mL 5% EtOH (v/v) in water (adjusted to pH 7) before use.

The cartridge was washed with 2 mL 50 mM sodium acetate and then the malodor causing volatile acid compounds eluted with 6 mL MeOH, followed by 6 mL MeOH with 2% (v/v) trifluoroacetic acid (TFA). The eluate from 6 mL MeOH with 2% TFA was then derivatized by 2 mL boron trifluoride (14% w/w) and heated at 60° C. for 3 h with continuous stirring. The reaction was then cooled to room temperature and 1 mL water was added to stop the reaction.

10 mL 0.5 M NaHCO$_3$ was added to neutralize TFA (pH 6-7). E3M2H and HMHA methyl esters were extracted twice by 10 mL CH$_2$Cl$_2$, and concentrated to 5 mL under N$_2$ for GC-MS/MS analysis with optimized MRM transitions.

Dynamic ranges, LOD, LOQ, Reproducibility and Recoveries: The target compound E3M2H methyl ester and HMHA methyl ester were quantified with the external standard curves, which composed of a series of 0.01, 0.1, 0.5, 1 and 5 μg/mL. The calibration curves for E3M2H methyl ester and HMHA methyl ester were separately y=28080x−108.88, R$^2$=0.9999, and y=200203x−2262, R$^2$=0.9999 and their working ranges were both 0.01-5 μg/mL (Table 3). LOD and LOQ were both 0.005 μg/mL and 0.01 μg/mL for E3M2H methyl ester and HMHA methyl ester (Table 3). High sensitivity was achieved for E3M2H and HMHA.

To investigate the recoveries, 0.5 μg, 1 μg and 5 μg E3M2H and HMHA were added to a t-shirt. Each experiment was repeated for three times and the recoveries with standard deviation are shown in Table 4. The recoveries of E3M2H were in the range of 93±7% to 103±4%, and the recoveries of HMHA were from 85±2% to 88±4% (Table 4).

Ten mg E3M2H methyl ester and 10 mg HMHA methyl ester samples were accurately weighed and transferred to a 50 mL volumetric flask. The samples were dissolved in 30 mL dichloromethane and the volume made up to 50 mL (200 μg/mL stock solution A). Ten mL of 200 μg/mL stock solution A was diluted to 20 mL for 100 μg/mL stock solution B. Five mL of 100 μg/mL stock solution B was diluted to 50 mL for 10 μg/mL stock solution C. Ten mL and 5 mL of 10 μg/mL stock solution C was separately diluted to 20 mL and 50 mL to obtain 5 μg/mL and 1 μg/mL standard solutions. Ten mL and 5 mL of 1 μg/mL standard solution were separately diluted to 20 mL and 50 mL to obtain 0.5 μg/mL and 0.1 μg/mL standard solutions. Ten mL and 5 mL of 0.1 μg/mL standard solution were separately diluted to 20 mL and 50 mL to obtain 0.05 μg/mL and 0.01 μg/mL standard solutions. Ten mL of 0.01 μg/mL standard solution was diluted to 20 mL for 0.005 μg/mL standard solution.

GC-MS/MS analysis was performed on a GCMS TQ8030 (Shimazu). Separation was achieved using a DB-WAX column (30 m×0.25 mm i.d.×0.25 μm film thickness, J & W Scientific, Agilent Technologies, Foster City, CA). The DB-WAX column using the following temperature program: 50° C. (held for 1 min), 50° C.-250° C. (25° C./min, held for 1 min). The injector temperature of GC was 250° C. and inject volume is 1 μL with splitless mode. The temperature of the ion source of the mass spectrometer was 200° C., and transfer line was heated at 230° C. Helium was used as carrier gas at a constant flow rate of 1.0 mL/min. Data were acquired in MRM mode and MRM parameters are shown below.

| Compound | Segments (min) | MRM transition | CE (eV) |
|---|---|---|---|
| E3M2H methyl ester | 2.00-5.65 | 142 > 127 | 9 |
| | | 142 > 83 | 12 |
| | | 142 > 95 | 12 |
| HMHA methyl ester | 5.65-7.00 | 145 > 71 | 6 |
| | | 117 > 85 | 6 |
| | | 85 > 43 | 9 |

TABLE 3

LOD, LOQ and dynamic range of E3M2H methyl ester, and HMHA methyl ester by GC-MS/MS (μg/mL)

| Compounds | LOD | LOQ | Dynamic range | Equation | R$^2$ |
|---|---|---|---|---|---|
| E3M2H methyl ester | 0.005 | 0.01 | 0.01-5 | y = 28080x − 108.88 | 0.9999 |
| HMHA methyl ester | 0.005 | 0.01 | 0.01-5 | y = 200203x − 2262 | 0.9999 |

TABLE 4

Recoveries of E3M2H and HMHA

| | Recoveries % (Average ± SD, n = 3) | | |
|---|---|---|---|
| Compounds | Added 0.5 μg | Added 1 μg | Added 5 μg |
| E3M2H | 96 ± 8% | 93 ± 7% | 103 ± 4% |
| HMHA | 88 ± 1% | 88 ± 4% | 85 ± 2% |

Sensory Evaluation: T-shirts worn for 24 hours by subjects were smelled and the intensity of axillary malodor was evaluated. The intensity was described as follows. 1. no bad odor 2. barely perceptible malodor. 3. very weak malodor. 4. weak malodor. 5. moderate malodor. 6. intense malodor. 7. very intense malodor. Amounts of E3M2H and HMHA were generally positively related and consistent with sensory evaluation.

Figure 8:
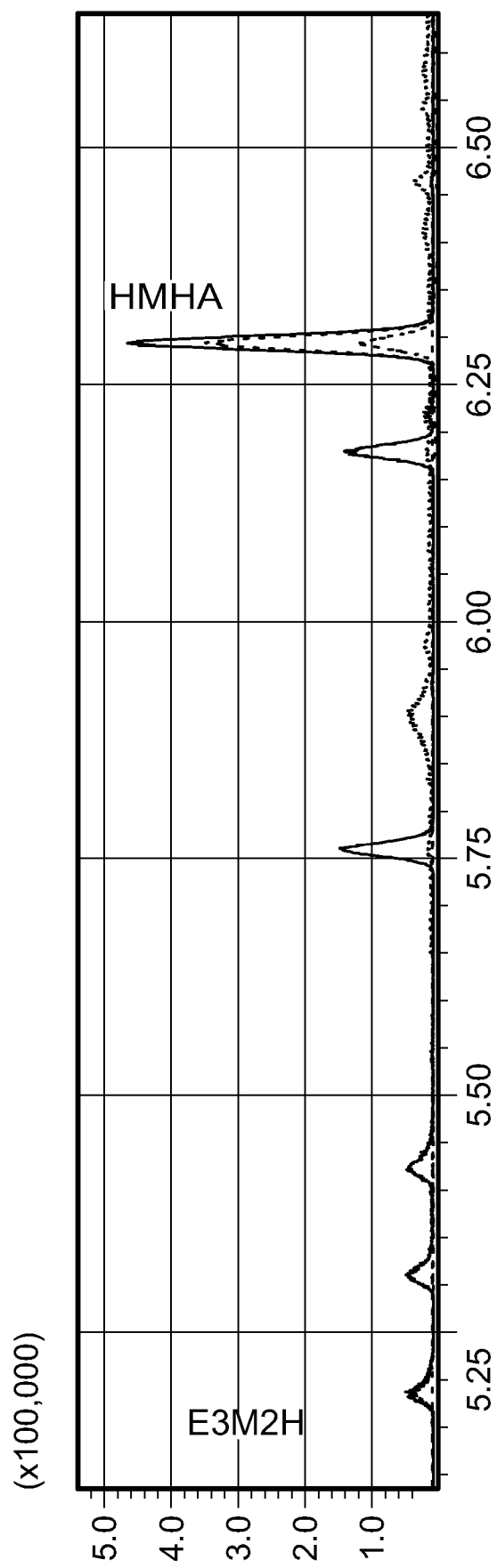
FIG. 8 shows a representative chromatogram obtained according to the methods presented herein.

E3M2H and HMHA were quantified from one side of worn t-shirt by 9 Caucasian subjects and results are shown in Table 5. An MRM chromatogram of axillary malodor adsorbed on t-shirt of a subject is shown in FIG. 8. E3M2H and HMHA were detected from all 9 Caucasian subjects. E3M2H ranged from 0.1 μg to 3.5 μg and HMHA ranged from 0.2 μg to 9.8 μg from one side of worn t-shirt by 9 subjects. To compare the results of headspace and the t-shirt collection from 9 subjects, collection of axillary malodor compounds by headspace promptly when subjects wore t-shirts after 24 hours. Individual subjects released high E3M2H collected by headspace also showed high amounts of E3M2H adsorbed on the t-shirts, except subject 7 (Table 2 and 5). The t-shirt of subject 7 was loose and most axillary acids did not retain on the t-shirt, did not well represent their amounts.

TABLE 5

Contents of E3M2H and HMHA detected from t-shirt and released from the axilla

| | | From one side of t-shirt | | Sensory evaluation |
|---|---|---|---|---|
| Subjects | Sex | E3M2H(μg) | HMHA (μg) | |
| 1 | Female | 0.08 | 0.28 | 3 |
| 2 | Male | 0.31 | 2.31 | 4 |
| 3 | Female | 0.08 | 0.24 | 3 |
| 4 | Male | 3.54 | 9.83 | 6 |
| 5 | Female | 0.27 | 0.23 | 4 |
| 6 | Male | 0.27 | 0.68 | 4 |
| 7 | Female | 0.61 | 1.42 | 5 |
| 8 | Male | 0.17 | 1.14 | 3 |
| 9 | Female | 0.56 | 1.49 | 3 |

Publications cited throughout this document are hereby incorporated by reference in their entirety. Although the various aspects of the invention have been illustrated above by reference to examples and preferred embodiments, it will be appreciated that the scope of the invention is defined not by the foregoing description but by the following claims properly construed under principles of patent law.

The invention claimed is:

1. A method,
wherein the method identifies compounds having the ability to prevent, treat, or reduce malodor development on body surfaces, the method comprising the steps of:
 a. contacting a subject with a test compound;
 b. collecting a sample comprising at least one malodor causing volatile compound directly from the headspace of the axilla of a subject, wherein the sample is an air sample, wherein the sample is collected using a sampling apparatus comprising a sampling cell and a sampling tube;
 c. adsorbing the collected sample onto an adsorbent material; and
 d. determining, in the adsorbed collected sample, the amount of at least one malodor causing volatile compound selected from the group consisting of: 3-methyl-2-hexenoic acid (3M2H), 3-hydroxy-3-methylhexanoic acid (HMHA), and 3-methyl-3-sulfanylhexan-1-ol (MSH),
wherein the determining step is performed by thermal desorption GC/MS, and
wherein the test compound prevents, treats, or reduces malodor development on body surfaces if the amount of the at least one malodor causing volatile compound is lower in the sample collected from the subject contacted with the test compound compared to the amount of the at least one malodor causing volatile compound in a sample collected from a non-treated subject.

2. The method according to claim 1, wherein the sampling apparatus is configured to draw air through the sampling cell and sampling tube.

3. The method according to claim 1, wherein surfaces of the sampling cell and sampling tube are deactivated prior to sample collection.

4. The method according to claim 1, wherein surfaces of the sampling cell and sampling tube are treated prior to sample collection with an agent that prevents, reduces, or inhibits the adsorption of the at least one malodor causing volatile compound to the surfaces of the sampling cell and sampling tube.

5. The method according to claim 1, wherein surfaces of the sampling cell and sampling tube are treated prior to sample collection with one or more treatments comprising contacting the surface of the sampling cell and sampling tube with dichlorodimethylsilane (DMDCS) in toluene followed by at least one rinse with toluene.

6. The method according to claim 1, wherein the sample is collected for up to about 60 minutes.

7. The method according to claim 1, wherein the sample is collected at an air flow rate in a range of from about 100 ml/min to about 200 ml/min.

8. The method according to claim 1, wherein the sample is collected by repeating the collection b) and adsorbing c) steps one or more times on the same axilla of the subject.

9. The method according to claim 1, wherein the sample is collected by repeating the collection b) and adsorbing c) steps one or more times on more than one axilla of the subject.

10. The method according to claim 1, wherein the determining step is performed by thermal desorption GC/MS and the at least one malodor causing volatile compound is quantified by selected ion monitoring (SIM) mode.

11. A method,
wherein the method identifies compounds having the ability to prevent, treat, or reduce malodor development on body surfaces, the method comprising the steps of:
 a. contacting a subject with a test compound;
 b. collecting a sample comprising at least one malodor causing volatile acid compound from a sample of clothing obtained from a subject;
 c. extracting the at least one malodor causing volatile acid compound from the collected sample of the subject's clothing with a solvent;
 d. forming an ester of the at least one malodor causing volatile acid compound, wherein the ester is an ester selected from the group consisting of methyl esters, ethyl esters, propyl esters, and butyl esters;
 e. extracting the ester of the at least one malodor causing volatile acid compound, thereby forming an extracted sample, and
 f. determining, in the extracted sample, the amount of at least one ester of the malodor causing volatile acid compound selected from the group consisting of: 3-methyl-2-hexenoic acid (3M2H), and 3-hydroxy-3-methylhexanoic acid (HMHA),
wherein the determining step is performed by GC-MS/MS, and
wherein the test compound prevents, treats, or reduces malodor development on body surfaces if the amount of the extracted ester of the at least one malodor causing volatile acid compound is lower in the sample collected from the subject contacted with the test compound compared to the amount of the extracted ester of the at least one malodor causing volatile acid compound in a sample collected from a non-treated subject.

12. The method according to claim 11, wherein the sample of clothing is an under-arm portion of the clothing.

13. The method according to claim 11, wherein the extraction further comprises sonication of the collected sample of the subject's clothing with a solvent.

14. The method according to claim 11, wherein the solvent comprises ethanol.

15. The method according to claim 11, wherein the ester is formed by reacting the extracted at least one malodor causing volatile acid compound with $BF_3$ and an alcohol selected from the group consisting of methanol, ethanol, propanol, and butanol.

16. The method according to claim 11, wherein the ester of the at least one malodor causing volatile acid compound is extracted by the addition of $CH_2Cl_2$ to form the extracted sample.

17. The method according to claim 11, wherein the ester of the at least one malodor causing volatile acid compound is extracted by the addition of a solvent selected from the group consisting of pentane, heptane, and cyclohexane.

18. The method according to claim 11, wherein the extracted sample is concentrated prior to the determining step performed by GC-MS/MS.

19. The method according to claim 11, wherein the determining step is performed by quantifying the amount of the at least one ester of the malodor causing volatile acid compound by GC-MS/MS with optimized MRM transitions.

* * * * *